(12) United States Patent
Nakata et al.

(10) Patent No.: US 8,687,850 B2
(45) Date of Patent: Apr. 1, 2014

(54) APPARATUS AND METHOD FOR DETERMINING KIND OF STEEL MATERIAL

(75) Inventors: Takeo Nakata, Osaka (JP); Masami Ikeda, Osaka (JP); Makoto Sakamoto, Osaka (JP); Kenji Fujiwara, Osaka (JP); Kazuhiro Uchida, Osaka (JP)

(73) Assignee: Nippon Steel & Sumitomo Metal Corporation, Tokyo (JP)

( * ) Notice: Subject to any disclaimer, the term of this patent is extended or adjusted under 35 U.S.C. 154(b) by 125 days.

(21) Appl. No.: 13/469,720

(22) Filed: May 11, 2012

(65) Prior Publication Data

US 2012/0281877 A1    Nov. 8, 2012

Related U.S. Application Data

(63) Continuation of application No. PCT/JP2010/062761, filed on Jul. 29, 2010.

(30) Foreign Application Priority Data

Nov. 20, 2009  (JP) .................................. 2009-264690

(51) Int. Cl.
  *G06K 9/00*  (2006.01)
(52) U.S. Cl.
  USPC ............ 382/103; 382/100; 382/141; 382/194
(58) Field of Classification Search
  USPC .................................. 382/100, 103, 141, 191
  See application file for complete search history.

(56) References Cited

U.S. PATENT DOCUMENTS

2003/0228066 A1*  12/2003  Tomita et al. ................. 382/274

FOREIGN PATENT DOCUMENTS

| JP | 02-132350 | 5/1990 |
|---|---|---|
| JP | 07-294438 | 11/1995 |
| JP | 07-294439 | 11/1995 |
| JP | 08-178834 | 7/1996 |
| JP | 08-247926 | 9/1996 |
| JP | 3482265 | 12/2003 |

OTHER PUBLICATIONS

Japanese Industrial Sstandard, Method of Spark Test for Steels, JIS G 0566, Japanese Standards Association, Jan. 5, 1980.

* cited by examiner

*Primary Examiner* — Tom Y Lu
(74) *Attorney, Agent, or Firm* — Clark & Brody (57) ABSTRACT

An apparatus 1 for determining a kind of a steel material detects a spark pixel from a color picked-up image 2 of a spark 19 produced when a steel material 18 is ground, and detects a pixel, in which the density of any one color component for judgment selected from among RGB color components is low, as a low-density pixel from the spark pixels. The apparatus 1 determines that the steel material is a steel material consisting of the high-strength steel if the ratio of the total number of low-density pixels to the total number of spark pixels is not lower than a threshold value for judgment, and determines that the steel material is a steel material consisting of the ordinary steel if the ratio is lower than the threshold value for judgment.

4 Claims, 5 Drawing Sheets

APPARATUS AND METHOD FOR DETERMINING KIND OF STEEL MATERIAL

TECHNICAL FIELD

The present invention relates to an apparatus and method for determining the kind of a steel material, by which it is judged whether the steel material is a steel material consisting of a high-strength steel containing an addition agent for improving the steel strength or is a steel material consisting of an ordinary steel in which the addition agent is not contained.

BACKGROUND ART

In a known method for determining the carbon content of steel material or making judgment of whether the steel material is a steel material consisting of a high-strength steel containing an addition agent for improving the steel strength or is a steel material consisting of an ordinary steel in which the addition agent is not contained, an inspector visually observes a spark produced when the steel material is ground by a grinder or the like, and the inspector makes determination or judgment from the state of spark observed. Some addition agents for improving the steel strength improve the steel strength by enhancing hardenability, solid solution effect, or the like. As a specific example of such an addition agent, V, Cr, Mo, Nb, Cu and Ni can be cited.

Unfortunately, the above-described method for determination or judgment poses a problem of the inconsistent accuracy of the determination or judgment, and also a skilled inspector is needed because the determination or the judgment result depends on the skill of inspector.

A steel material inspection apparatus for making the above-described determination stably and accurately has been proposed (for example, refer to JP3482265B). Unfortunately, the steel material inspection apparatus described in JP3482265B cannot be used to make the above-described judgment stably and accurately. Therefore, it is still desired to develop an apparatus and method capable of making the above-described judgment stably and accurately.

SUMMARY OF INVENTION

Accordingly, an object of the present invention is to provide an apparatus and method for determining the kind of a steel material, by which it can be judged stably and accurately whether the steel material is a steel material consisting of a high-strength steel containing an addition agent for improving the steel strength or is a steel material consisting of an ordinary steel in which the addition agent is not contained.

The present invention provides an apparatus for determining the kind of a steel material, comprising: an image pickup device for imaging a spark, which is produced when the steel material is ground, continuously a plurality of times to produce a plurality of color picked-up images; a detection device for detecting a spark pixel corresponding to a spark from each of the color picked-up images produced by the image pickup device, and for detecting a pixel, in which the density of any one color component for judgment selected from among RGB color components is lower than a first density threshold value, as a low-density pixel from the detected spark pixels; a calculation device for calculating the total number of spark pixels and the total number of low-density pixels by summing up the number of spark pixels and the number of low-density pixels of each color picked-up image detected by the detection device, respectively, for all of the color picked-up images, and for calculating the ratio of the total number of the low-density pixels to the total number of the spark pixels; and a judgment device for determining that the steel material is a steel material consisting of a high-strength steel containing an addition agent for improving the steel strength if the ratio is not lower than a threshold value for judgment, and determining that the steel material is a steel material consisting of an ordinary steel in which the addition agent is not contained if the ratio is lower than the threshold value for judgment.

Herein, RGB means three colors of Red, Green, and Blue.

The color component for judgment refers to one component of the RGB color components selected to judge whether the steel material is a steel material consisting of a high-strength steel containing an addition agent for improving the steel strength or is a steel material consisting of an ordinary steel in which the addition agent is not contained.

The first density threshold value is a threshold value for detecting a low-density pixel from the spark pixels.

The threshold value for judgment is a threshold value for judging whether the steel material is a steel material consisting of a high-strength steel containing an addition agent for improving the steel strength or is a steel material consisting of an ordinary steel in which the addition agent is not contained.

As described above, according to the kind determining apparatus in accordance with the present invention, based on the magnitude relationship between the ratio of the total number of low-density pixels to the total number of spark pixels (hereinafter, referred to as a "low-density pixel occupation ratio" when deemed appropriate) and the threshold value for judgment, it is automatically judged whether the steel material is a steel material consisting of a high-strength steel containing an addition agent for improving the steel strength or a steel material consisting of an ordinary steel in which the addition agent is not contained. Therefore, according to the kind determining apparatus in accordance with the present invention, since the judgment result does not depend on the skill of inspector who makes judgment, the judgment can be made stably. As the addition agent for improving the steel strength, an addition agent that improves the steel strength by enhancing hardenability, solid solution effect, or the like can be cited, and as a specific example of such an addition agent, V, Cr, Mo, Nb, Cu and Ni can be cited.

In the spark produced when the steel material consisting of a high-strength steel containing an addition agent for improving the steel strength or the steel material consisting of an ordinary steel in which the addition agent is not contained is ground, there exists a low-density part in which the density of any one specific color component selected from among the RGB color components is low. Comparing the spark produced when the steel material consisting of a high-strength steel containing an addition agent for improving the steel strength is ground and the spark produced when the steel material consisting of an ordinary steel in which the addition agent is not contained is ground, the spark produced when the steel material consisting of a high-strength steel is ground has a higher ratio of the low-density part to the whole of the spark. In other words, comparing the spark produced when the steel material consisting of a high-strength steel containing an addition agent for improving the steel strength is ground and the spark produced when the steel material consisting of an ordinary steel to which the addition agent is not contained is ground, the spark produced when the steel material consisting of a high-strength steel is ground has a higher low-density pixel occupation ratio.

The low-density pixel occupation ratios in the spark produced when the steel material consisting of a high-strength steel containing an addition agent for improving the steel strength is ground and the spark produced when the steel material consisting of an ordinary steel in which the addition agent is not contained is ground are examined in advance, and the threshold value for judgment for judging the high-strength steel and the ordinary steel is set to the low-density pixel occupation ratio. Thereby, the kind determining apparatus in accordance with the present invention can judge accurately whether the steel material is a steel material consisting of a high-strength steel containing an addition agent for improving the steel strength or is a steel material consisting of an ordinary steel in which the addition agent is not contained.

In the color picked-up image of the spark produced when the steel material consisting of a high-strength steel containing an addition agent for improving the steel strength is ground or the steel material consisting of an ordinary steel in which the addition agent is not contained is ground, in addition to the spark zone corresponding to the spark, there exist a periphery zone located around the spark zone and a background zone that is a zone in which the background image of spark is displayed. The color density of the spark zone is basically higher than the color densities of the periphery zone and the background zone. Therefore, as a method for detecting the spark pixel used for the calculation of the above-described low-density pixel occupation ratio from the color picked-up image, binarization of the spark pixel and other pixels is conceivable.

However, since the brightness of spark differs from spark to spark, in the case where a plurality of spark zones corresponding to a plurality of sparks are present on one sheet of color picked-up image, the color density differs between spark zones. Also, there is a tendency such that with an increase in the color density of a spark zone, the color density of the periphery zone located around the spark zone increases. The color density of the periphery zone having a high color density may become higher than that of the spark zone having a low color density. Therefore, if the above-described threshold value for binarization is set at a color density lower than the color density of the spark zone having a low color density, there is a fear that even a pixel constituting the periphery zone having a high color density is detected as spark pixel. On the other hand, if the threshold value for binarization is set at a density higher than the density of the periphery zone having a high density, there is a fear that a spark pixel constituting the spark zone having a low density is not detected as a spark pixel.

For detecting the spark zone accurately, it is preferable that the detection device performs: first processing in which a spark candidate pixel group consisting of pixels, which are continuous with each other along each of pixel lines constituting each of the color picked-up images and in which the density of any one color component for detection selected from among the RGB color components is not lower than a second density threshold value, is detected from each of pixel lines of each of the color picked-up images; and second processing in which the highest density of the color component for detection of pixels constituting the spark candidate pixel group is detected, and a pixel, in which the density of the color component for detection is lower than the highest density and is not lower than a third density threshold value larger than the second density threshold value, is detected as the spark pixel from the pixels constituting each of the spark candidate pixel groups.

Herein, the pixel line means a row of pixels connected linearly from one end side of picked-up image to the other end side thereof in the transverse or longitudinal direction of the picked-up image, in which the number of pixels in the width direction of row is one.

The color component for detection refers to one component of the RGB color components selected to detect the spark candidate pixel group from the picked-up image.

The second density threshold value is a threshold value of pixel density that is set to detect the spark candidate pixel group from the picked-up image.

The spark candidate pixel group is a group of pixels having a possibility of being in the spark zone.

The third density threshold value is a threshold value of pixel density that is set to detect the pixels constituting the spark pixel group from the pixels constituting the spark candidate pixel group.

The first processing is processing for detecting the spark candidate pixel group consisting of pixels, which are continuous with each other along the pixel line constituting each of the color picked-up images and in which the density of any one color component selected from among the RGB color components is not lower than the second density threshold value, from each of the pixel lines in each of the color picked-up images. Basically, the density of the color component for detection is the highest in the spark zone, next higher in the periphery zone, and the lowest in the background zone.

If the upper limit value that the second density threshold value used in the first processing can take is made not higher than the density of color component for detection of the spark zone in which the density of color component for detection is the lowest, the omission of the spark zone having a low density from the pixels detected as the spark candidate pixel group can be prevented. Also, by making the lower limit value that the second density threshold value can take higher than the density of color component for detection of the pixel, in which the density of color component for detection is the highest of the pixels constituting the background zone, the detection of the pixels constituting the background zone as the pixels constituting the spark candidate pixel group can be excluded. However, like the color density of spark zone, the density of color component for detection of the spark zone differs between spark zones. As the density of color component for direction of the spark zone increases, the density of color component for detection of the periphery zone located around that spark zone tends to increase. In some cases, the density of color component for detection of the periphery zone in which the density of color component for detection is high becomes higher than that of the spark zone in which the density of color component for detection is low. Therefore, in the case where the second density threshold value is set between the above-described upper limit value and lower limit value, if a periphery zone in which the density of color component for detection is higher than that of the spark zone exists, the pixels constituting the periphery zone are detected as the pixels constituting the spark candidate pixel group together with the spark pixels constituting the spark zone around which the periphery zone is located.

The second processing is processing for detecting the highest density of color component for detection of pixels constituting each of the spark candidate pixel groups and for detecting the pixel, in which the density of color component for detection is lower than the highest density and is not lower than the third density threshold value larger than the second density threshold value, as the spark pixel from the pixels constituting each of the spark candidate pixel groups. The spark zone has a higher density of a color component for detection than the periphery zone located around the spark zone. Even if the pixels constituting the spark zone and the pixels constituting the periphery zone located around the spark zone are detected as the spark candidate pixel group, by setting the third density threshold value between the density of a color component for detection of the pixel constituting the periphery zone and the density of a color component for detection of the spark pixel constituting the spark zone, the detection of the pixels constituting the periphery zone as the spark pixels can be excluded. That is, thereby, the spark pixel can be detected accurately from the color picked-up image.

Since the second processing is performed for each of the spark candidate pixel groups, the individual third density threshold value can be set for each second processing for each of the spark candidate pixel groups. Therefore, even if the density of color component for detection differs between the spark zones constituting each of the spark candidate pixel groups, the third density threshold value can be set between the density of color component for detection of the spark zone constituting each of the spark candidate pixel groups and the density of color component for detection of the periphery zone, so that the spark pixel can be detected accurately from the pixels constituting each of the spark candidate pixel groups.

And the present invention provides a method for determining the kind of a steel material, comprising: an imaging step of imaging a spark, which is produced when the steel material is ground, continuously a plurality of times to produce a plurality of color picked-up images; a detecting step of detecting a spark pixel corresponding to a spark from each of the color picked-up images produced in the imaging step, and detecting a pixel, in which the density of any one color component for judgment selected from among RGB color components is lower than a first density threshold value, as a low-density pixel from the detected spark pixel; a calculating step of calculating the total number of spark pixels and the total number of low-density pixels by summing up the number of spark pixels and the number of low-density pixels of each color picked-up image detected in the detecting step, respectively, for all of the color picked-up images, and calculating the ratio of the total number of the low-density pixels to the total number of the spark pixels; and a judging step of determining that the steel material is a steel material consisting of a high-strength steel containing an addition agent for improving the steel strength if the ratio is not lower than a threshold value for judgment, and determining that the steel material is a steel material consisting of an ordinary steel in which the addition agent is not contained if the ratio is lower than the threshold value for judgment.

It is preferable that wherein in the imaging step, a spark produced when the steel material is ground by a grinding member pressed against the steel material with a force not lower than 2.94 N and not higher than 9.8 N is imaged.

If the force with which the grinding member is pressed against the steel material is made not lower than 2.94 N, the number of alloy sparks produced is stabilized. Therefore, according to this preferable method, it can be judged stably whether the steel material consists of a high-strength steel containing an addition agent for improving the steel strength or an ordinary steel in which the addition agent is not contained. Also, if the pressing force is made not higher than 9.8 N, the steel material can be ground without the occurrence of deep flaws on the steel material. Therefore, according to the above-described preferable method, the aforementioned judgment can be made stably and accurately without the occurrence of deep flaws on the steel material.

The present invention is able to provide an apparatus and method for determining the kind of a steel material, by which it can be judged stably and accurately whether the steel material is a steel material consisting of a high-strength steel containing an addition agent for improving the steel strength or is a steel material consisting of an ordinary steel in which the addition agent is not contained.

DESCRIPTION OF EMBODIMENTS

Hereunder, explanation is given of judgment whether a steel material consists of a high-strength steel containing an addition agent for improving the steel strength ((hereinafter, referred to as a "high-strength steel" when deemed appropriate) or an ordinary steel in which the addition agent is not contained (hereinafter, referred to as an "ordinary steel" when deemed appropriate) made by using an apparatus for determining the kind of the steel material (hereinafter, referred to a "kind determining apparatus") of this embodiment.

Figure 1:
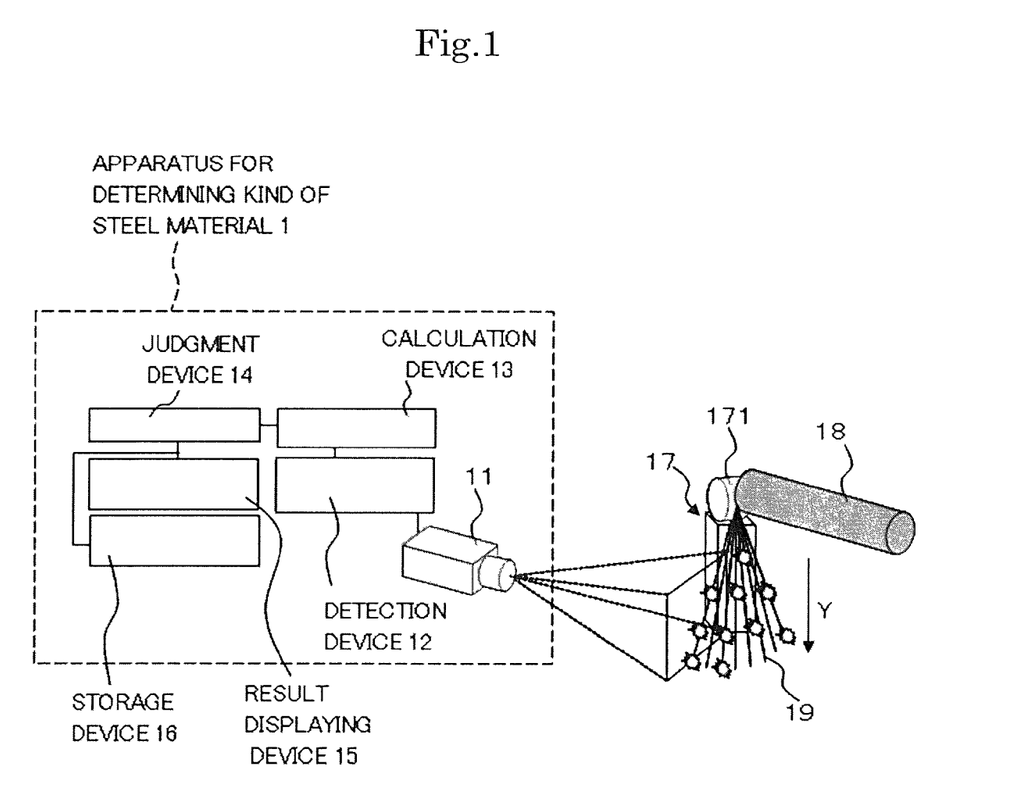
FIG. 1 is a schematic view of the kind determining apparatus of this embodiment.

FIG. 1 is a schematic view of the kind determining apparatus of this embodiment. As shown in FIG. 1, the kind determining apparatus 1 includes an image pickup device 11. A grinding member (a grinder 17 in this embodiment) is pressed against a steel material 18, and a spark 19 produced from the steel material 18 by grinding is imaged continuously a plurality of times to produce a plurality of color picked-up images by the image pickup device 11. A force with which the grinder 17 is pressed against the steel material 18 is not lower than 2.94 N and not higher than 9.8 N. The circumferential speed of the grindstone of the grinder 17 is 30 m/sec. The exposure time of the image pickup device 11 is 4 msec. The image pickup device 11 continuously images the spark 19 twenty times at time intervals of 50 msec within 1 sec.

Figure 2:
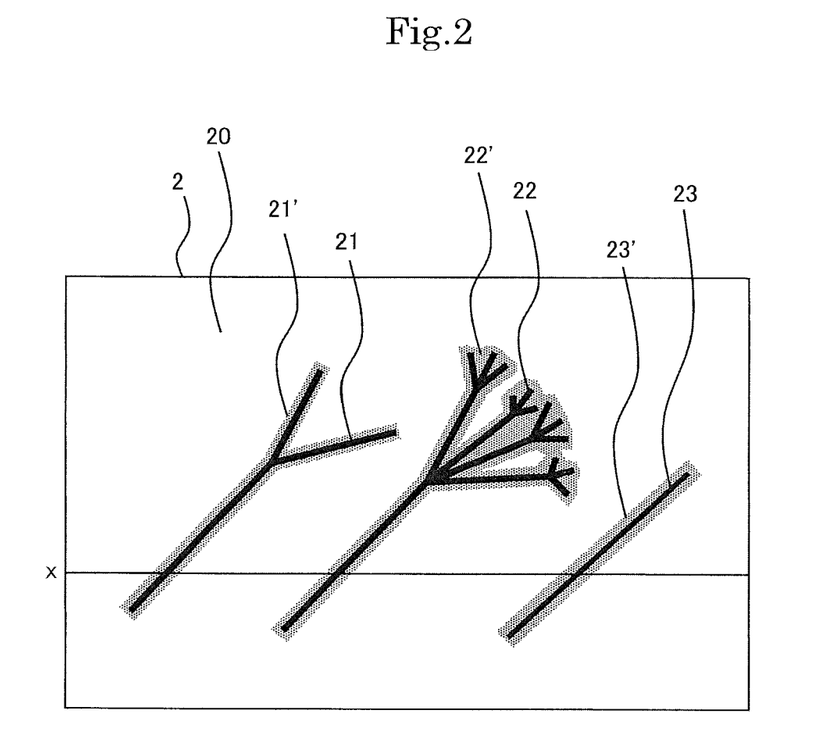
FIG. 2 is a schematic view of a color picked-up image picked up by the image pickup device.

FIG. 2 is a schematic view of a color picked-up image 2 picked up by the image pickup device 11. The color picked-up image 2 is configured so that M number of pixel lines, each of which is configured by arranging N number of pixels in the right and left direction in FIG. 2, are arranged in the up and down direction in FIG. 2. In the color picked-up image 2, there exist spark zones 21, 22 and 23 formed by the spark pixels corresponding to the spark 19, periphery zones 21', 22' and 23' located at the periphery of each of the spark zones 21, 22 and 23, and a background zone which is distant from the spark zones 21, 22 and 23. In FIG. 2, the spark zones 21, 22 and 23 are displayed in black, the periphery zones 21', 22' and 23' are displayed in gray, and the background zone 20 is displayed in white. Further, in the spark produced when the steel material 18 is ground, there exists a low-density part in which the density of any one specific color component selected from among RGB color components is lower than in other parts in the spark. In the spark zones 21, 22 and 23 of the color picked-up image 2, a low-density zone corresponding to the aforementioned low-density part exists.

The image pickup device 11 sends the produced color picked-up images 2 to a detection device 12.

Upon receipt of the color picked-up image 2 from the image pickup device 11, the detection device 12 performs first processing. The first processing is processing for detecting a spark candidate pixel group consisting of pixels which are continuous with each other along each pixel line and in which the density of any one color component for detection selected from among the RGB color components is not lower than a second threshold value. As the color component for detection, a component having the highest density is preferably selected from among the RGB color components that the spark 19 has. A high density increases the difference between the density of spark zone and the density of background zone, so that the subsequent detection of spark candidate pixel group and spark pixel can be made easily. In this embodiment, in each of the spark zones, an R color component having the highest density is adopted as the color component for detection.

Figure 3:
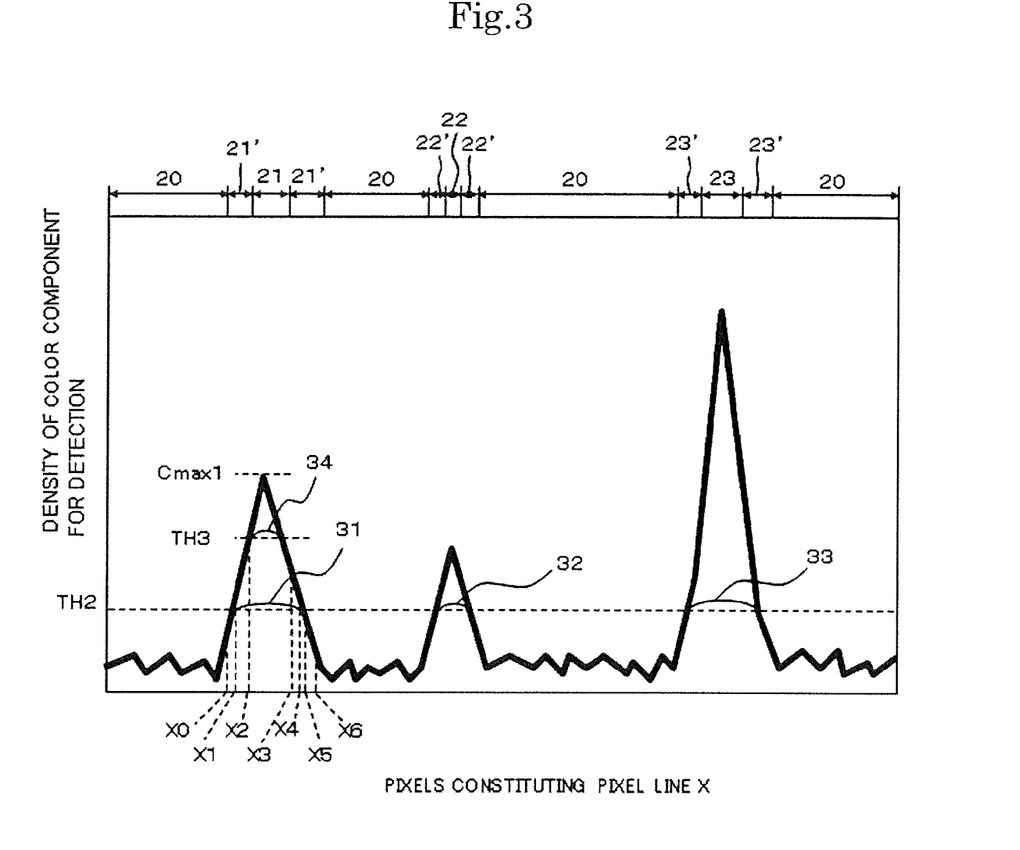
FIG. 3 is a graph showing the density distribution of a color component for detection of the pixel line X.

Hereunder, a scene in which the spark candidate pixel group is detected from a pixel line X (refer to FIG. 2) by the first processing is explained. FIG. 3 is a graph showing the density distribution of the color component for detection (R color component) of the pixel line X in FIG. 2. As shown in FIG. 2, on the pixel line X, there exist spark zones 21, 22 and 23 and periphery zones 21', 22' and 23' and background zone 20. As shown in FIG. 3, each of the spark zones 21, 22 and 23 has a higher density of a color component for detection in the color pick-up image 2 than each of the periphery zones 21', 22' and 23' located at the periphery of each of the spark zones 21, 22 and 23, and a background zone 20 has a lower density of a color component for detection than any of the spark zones 21, 22 and 23 and any of the periphery zones 21', 22' and 23'. The densities of a color component for detection of the spark zones 21, 22 and 23 differ from each other.

As shown in FIG. 3, a pixel X0 and a pixel X2 existing on the right-hand side of the pixel X0 in the figure and the pixels located between a pixel X0 and a pixel X2 constitute the periphery zone 21'. Also, a pixel X3 existing on the right-hand side of the pixel X2 on the pixel line X and a pixel X6 existing on the right-hand side of the pixel X3 on the pixel line X and the pixels located between the pixel X3 and the pixel X6 constitute the periphery zone 21'. Also, the pixels located between the pixel X2 and the pixel X3 (not including the pixel X2 and the pixel X3) constitute the spark zone 21.

At the time of the above-described first processing, the detection device 12 first determines whether or not the density of the color component for detection of each of the pixels constituting the pixel line X is not lower than the second density threshold value TH2 in the order from a pixel close to the end portion on one side (in this embodiment, the left-hand side in FIG. 3) of the pixel line X.

This second density threshold value TH2 is a density not higher than the lowest density of the densities of the color components for detection that each of the spark pixels constituting the spark zones 21, 22 and 23 has, and is a density higher than the highest density of the densities of the color components for detection that each of pixels constituting the background zone 20 has. As a method for setting the second density threshold value TH2 at a density in the above-described range, there can be cited, for example, a method in which the density slightly exceeding the highest density of the densities of the color components for detection that the pixels constituting the color picked-up image 2 picked up by the image pickup device 11 when no spark is produced have is set at the second threshold value TH2.

As shown in FIG. 3, of the pixels that constitute the pixel line X and have a density of the color components for detection not lower than the second density threshold value TH2, the pixel closest to the end portion on one side of the pixel line X is a pixel X1 located between the pixel X0 and the pixel X2. Therefore, the detection device 12 first detects the pixel X1 as a pixel having a density of the color components for detection not lower than the second density threshold value TH2. The detection device 12 recognizes the first detected pixel X1 as a start point pixel that is a pixel at which the detection of spark candidate pixel group is started.

After the pixel X1 has been recognized as the start point pixel, the detection device 12 determines whether or not the density of the color components for detection of each of the pixels existing on the other side of the start point pixel X1 on the pixel line X is lower than the second density threshold value TH2 in the order from a pixel close to the start point pixel X1. As shown in FIG. 3, among the pixels existing on the other side of the start point pixel X1 on the pixel line X, of the pixels having a density of the color components for detection lower than the second density threshold value TH2, the pixel closest to the start point pixel X1 is a pixel X5 located between the pixel X3 and the pixel X6. Therefore, the detection device 12 first detects the pixel X5 as a pixel having a density of the color components for detection lower than the second density threshold value TH2. The detection device 12 recognizes a pixel X4 adjacent to the detected pixel X5 on one side of the pixel X5 on the pixel line X as an end point pixel that is a pixel at which the detection of spark candidate pixel group is finished. The detection device 12 detects a pixel group formed by the start point pixel X1, the end point pixel X4, and the pixels existing between the start point pixel X1 and the end point pixel X4 as a spark candidate pixel group 31 (refer to FIG. 3).

If the second density threshold value TH2 is set at the above-described value, the detection of the pixels constituting the background zone as the pixels constituting the spark candidate pixel group can be excluded, and also the omission of spark pixels having a low density from the pixels detected as the spark candidate pixel group can be prevented.

After detecting the spark candidate pixel group 31, the detection device 12 recognizes start point pixels and end point pixels and detects other spark candidate pixel groups from among the pixels existing on the other side of the end point pixel X4 on the pixel line X. In this embodiment, the detection device 12 detects a spark candidate pixel group 32 formed by the pixels constituting the spark zone 22 and the pixels constituting the periphery zone 22' and a spark candidate pixel group 33 formed by the pixels constituting the spark zone 23 and the pixels constituting the periphery zone 23'.

After finishing the first processing, the detection device 12 performs second processing of all of the spark candidate pixel groups detected. The second processing is performed on each of the spark candidate pixel groups. In the second processing, the spark pixels are detected from the pixels constituting each of the spark candidate pixel groups.

Hereunder, the second processing performed on the spark candidate pixel group 31 is explained. As shown in FIG. 3, the detection device 12 binarizes the pixels constituting the spark candidate pixel group 31 by means of a third density threshold value TH31 that is lower than the highest density Cmax1 of the color component for detection of the pixels constituting the spark candidate pixel group 31 and exceeds the second density threshold value TH2. The detection device 12 detects the pixels having a density of the color component for detection not lower than the third density threshold value TH31 as a spark pixel. In this embodiment, the third density threshold value TH31 is set at a density higher than the highest value of the densities of the color component for detection that the pixels constituting the periphery zone 21' have, and is not higher than the lowest value of the densities of the color component for detection that the pixels constituting the spark zone 21 have. Therefore, the inclusion of the pixels constituting the periphery zone 21' in the pixels detected as the spark pixel by the second processing is excluded, so that the spark pixel can be detected accurately. The third threshold value TH3 can be calculated as described below. The ratio of the lowest density of the densities of color components for detection that each of the spark pixels constituting the spark zone has to the highest density is acquired in advance by sample examination, a value slightly lower than the acquired ratio is stored in the detection device 12, and the detection device 12 calculates the third threshold value TH3 by multiplying the value stored as the highest density.

Since the second processing is performed on each of the spark candidate pixel groups, individual third density threshold values can be set for each second processing performed on each of the spark candidate pixel groups. Therefore, even if the density of the color component for detection of spark zone constituting each of the spark candidate pixel groups differs, in the second processing performed on each of the spark candidate pixel groups, the third density threshold value can be set between the spark zone and the periphery zone, and the pixels constituting the spark zone can be detected from each of the spark candidate pixel groups.

After finishing the second processing, the detection device 12 detects a low-density pixel, in which the density of any one color component for judgment selected from among the RGB color components is lower than a first density threshold value, from the spark pixels detected by the second processing. In the selection of the color component for judgment, it is preferable that the extent of the low-density zone in each of the RGB color components be examined in advance for each of the addition agents for improving the steel strength, and a component in which the low-density zone is the most extensive be selected. The densities of the color components for detection that the spark pixels of the high-strength steel and the ordinary steel have are examined, and the first density threshold value is defined so that it is determined, by the later-described low-density pixel occupation ratio, whether the steel material 18 is a steel material consisting of a high-strength steel or a steel material consisting of an ordinary steel.

A calculation device 13 calculates the total number of spark pixels and the total number of low-density pixels that are detected by the detection device 12. Then, the calculation device 13 calculates the ratio of the total number of the calculated low-density pixels to the total number of the calculated spark pixels (the low-density pixel occupation ratio).

In the case where the low-density pixel occupation ratio calculated by the calculation device 13 is not lower than the threshold value for judgment, a judgment device 14 judges that the steel material 18 is a steel material consisting of a high-strength steel, and in the case where the low-density pixel occupation ratio calculated by the calculation device 13 is lower than the threshold value for judgment, the judgment device 14 judges that the steel material 18 is a steel material consisting of an ordinary steel. The spark produced when the high-strength steel is ground has a higher ratio of the low-density part to the whole spark than the spark produced when the ordinary steel is ground. Therefore, comparing the spark produced when the high-strength steel is ground and the spark produced when the ordinary steel is ground, the spark produced when the high-strength steel is ground has a higher low-density pixel occupation ratio. The low-density pixel occupation ratios of the color components for judgment that the spark pixels of the high-strength steel and the ordinary steel have are examined, and the threshold value for judgment is defined so that it is determined whether the steel material 18 is a steel material consisting of a high-strength steel or a steel material consisting of an ordinary steel. Therefore, according to the kind determining apparatus 1, it can be judged whether the steel material 18 is a steel material consisting of a high-strength steel or a steel material consisting of an ordinary steel.

Figure 4:
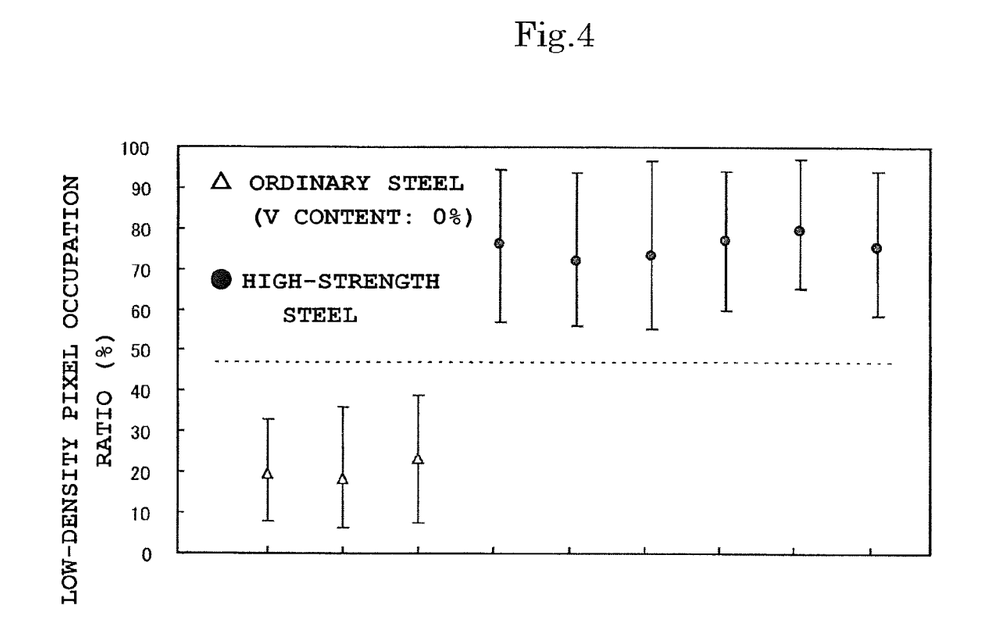
FIG. 4 is a graph showing the low-density pixel occupation ratios of the sparks produced when the steel material consisting of a high-strength steel are ground and the sparks produced when the steel material consisting of an ordinary steel are ground.

As an example of comparison of the low-density pixel occupation ratio of the spark produced when the high-strength steel is ground and that of the spark produced when the ordinary steel is ground, the low-density pixel occupation ratios of the high-strength steel containing an addition agent (V in this example) for improving the steel strength and the ordinary steel in which the addition agent is not contained are shown in FIG. 4. FIG. 4 shows the low-density pixel occupation ratios of the sparks produced when six steel materials each consisting of a high-strength steel are ground and the sparks produced when three steel materials each consisting of an ordinary steel are ground. In the case where the addition agent is V, B color is preferable as the color component for judgment. The low-density pixel occupation ratio shown in FIG. 4 is a ratio of low-density pixels in which the density of B color component is lower than a predetermined value to the total number of spark pixels (hereinafter, referred to as a "low-density pixel occupation ratio of B color component"). As shown in FIG. 4, comparing the sparks produced when the steel material consisting of a high-strength steel is ground and the sparks produced when the steel material consisting of an ordinary steel is ground, the sparks produced when the steel material consisting of a high-strength steel is ground have a higher low-density pixel occupation ratio of B color component. If the B color component is selected as the color component for judgment, the kind determining apparatus 1 can judge whether the steel material is a steel material consisting of a high-strength steel containing an addition agent for improving the steel strength or is a steel material consisting of an ordinary steel in which the addition agent is not contained based on the low-density pixel occupation ratio of B color component and the threshold value for judgment.

Thus, according to the kind determining apparatus 1, based on the magnitude relationship between the low-density pixel occupation ratio and the threshold value for judgment, it is automatically judged whether the steel material is a steel material consisting of a high-strength steel or a steel material consisting of an ordinary steel. Therefore, according to the kind determining apparatus 1, since the judgment result does not depend on the skill of inspector, the judgment can be made stably.

By using the judgment device 14, the result of judgment is displayed on a result displaying device 15 such as a monitor, or is stored in a storage device 16 such as a hard disk, memory, or the like.

Figure 5:
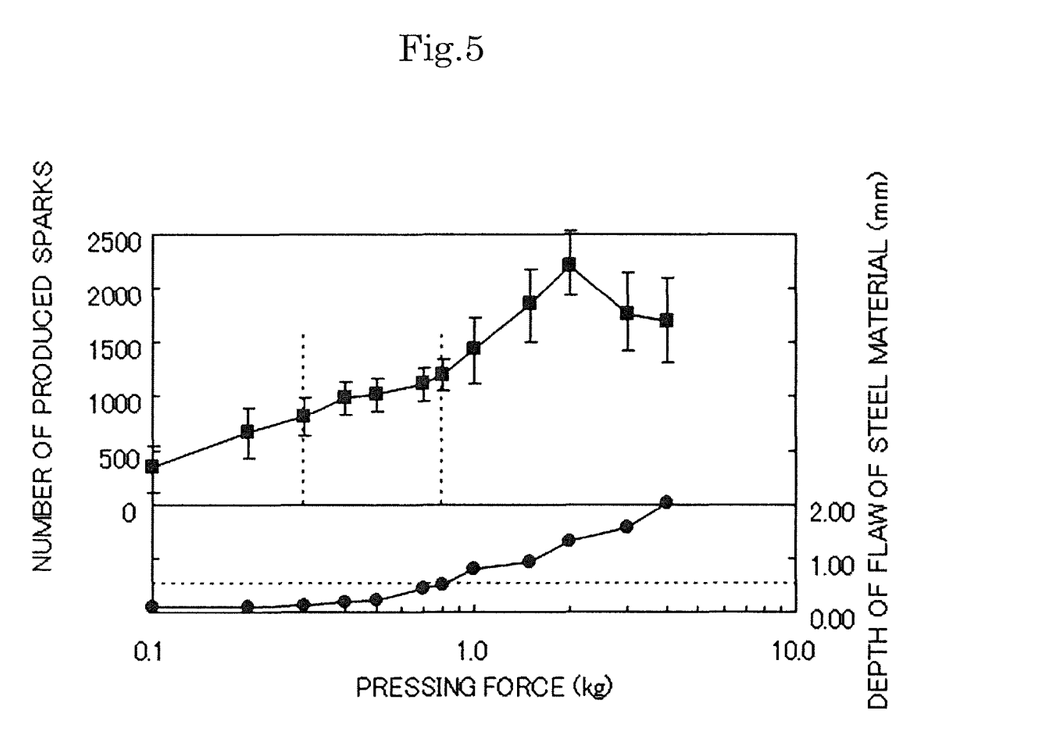
FIG. 5 is a graph showing the relationship between the pressing force of the peripheral face of the grindstone of a grinder against a steel material and the number of produced sparks and the depth of a flaw induced in the steel material.

As described above, in this embodiment, the force with which the grinder 17 is pressed against the steel material 18 is not lower than 2.94 N and not higher than 9.8 N. If the force with which the grinder 17 is pressed against the steel material 18 is made not lower than 2.94 N, as shown in FIG. 5, the number of produced sparks is stabilized. Therefore, by setting the force with which the grinder 17 is pressed against the steel material 18 within the above-described range, whether the steel material consists of a carbon steel or a low-alloy steel can be judged stably and accurately. If the pressing force is made not higher than 9.8 N, as shown in FIG. 5, the steel material 18 can be ground without the occurrence of deep flaws in the steel material 18. Therefore, by setting the force with which the grinder 17 is pressed against the steel material 18 within the above-described range, the above-described judgment can be made stably and accurately without the occurrence of deep flaws in the steel material 18.

As described above, in this embodiment, as the color component for detection, the R color component having the highest density in the spark zone of the RGB color components is used. Thereby, as compared with the case where any other color component is used as the color component for detection, in the density of the color component for detection, the possibility of overlapping of ranges that the spark zone and the periphery zone or other zones can take is reduced. Therefore, in the first processing, the detection of the pixels in other zones as the pixels constituting the spark candidate pixel group can be excluded surely, and also, in the second processing, the detection of the pixels constituting the periphery zone as the spark pixels can be excluded surely.

The invention claimed is:

1. An apparatus for determining the kind of a steel material, comprising:
    an image pickup device for imaging a spark, which is produced when the steel material is ground, continuously a plurality of times to produce a plurality of color picked-up images;
    a detection device for detecting a spark pixel corresponding to a spark from each of the color picked-up images produced by the image pickup device, and for detecting a pixel, in which the density of any one color component for judgment selected from among RGB color components is lower than a first density threshold value, as a low-density pixel from the detected spark pixels;
    a calculation device for calculating the total number of spark pixels and the total number of low-density pixels by summing up the number of spark pixels and the number of low-density pixels of each color picked-up image detected by the detection device, respectively, for all of the color picked-up images, and for calculating the ratio of the total number of the low-density pixels to the total number of the spark pixels; and
    a judgment device for determining that the steel material is a steel material consisting of a high-strength steel containing an addition agent for improving the steel strength if the ratio is not lower than a threshold value for judgment, and determining that the steel material is a steel material consisting of an ordinary steel in which the addition agent is not contained if the ratio is lower than the threshold value for judgment.

2. The apparatus for determining the kind of a steel material according to claim 1, wherein
    the detection device performs:
    first processing in which a spark candidate pixel group consisting of pixels, which are continuous with each other along each of pixel lines constituting each of the color picked-up images and in which the density of any one color component for detection selected from among the RGB color components is not lower than a second density threshold value, is detected from each of pixel lines of each of the color picked-up images; and
    second processing in which the highest density of the color component for detection of pixels constituting the spark candidate pixel group is detected, and a pixel, in which the density of the color component for detection is lower than the highest density and is not lower than a third density threshold value larger than the second density threshold value, is detected as the spark pixel from the pixels constituting each of the spark candidate pixel groups.

3. A method for determining the kind of a steel material, comprising:
    an imaging step of imaging a spark, which is produced when the steel material is ground, continuously a plurality of times to produce a plurality of color picked-up images;
    a detecting step of detecting a spark pixel corresponding to a spark from each of the color picked-up images produced in the imaging step, and detecting a pixel, in which the density of any one color component for judgment selected from among RGB color components is lower than a first density threshold value, as a low-density pixel from the detected spark pixel;
    a calculating step of calculating the total number of spark pixels and the total number of low-density pixels by summing up the number of spark pixels and the number of low-density pixels of each color picked-up image detected in the detecting step, respectively, for all of the color picked-up images, and calculating the ratio of the total number of the low-density pixels to the total number of the spark pixels; and
    a judging step of determining that the steel material is a steel material consisting of a high-strength steel containing an addition agent for improving the steel strength if the ratio is not lower than a threshold value for judgment, and determining that the steel material is a steel material consisting of an ordinary steel in which the addition agent is not contained if the ratio is lower than the threshold value for judgment.

4. The method for determining the kind of a steel material according to claim 3, wherein in the imaging step, a spark produced when the steel material is ground by a grinding member pressed against the steel material with a force not lower than 2.94 N and not higher than 9.8 N is imaged.

* * * * *